United States Patent [19]

Tanis et al.

[11] Patent Number: 5,105,013

[45] Date of Patent: Apr. 14, 1992

[54] METHOD FOR THE REDUCTIVE METHYLATION OF PRIMARY AMINES

[75] Inventors: Maarten Tanis, Hulst, Netherlands; Govind Rauniyar, Rixensart, Belgium

[73] Assignee: The Dow Chemical Company, Midland, Mich.

[21] Appl. No.: 286,419

[22] Filed: Dec. 19, 1988

[51] Int. Cl.⁵ .......................................... C07C 209/36
[52] U.S. Cl. ................................. 564/473; 544/402; 564/305; 564/397; 564/446; 564/503; 564/511; 564/512
[58] Field of Search ............... 564/473, 446, 305, 397, 564/503, 511, 512; 544/404, 402

[56] References Cited

U.S. PATENT DOCUMENTS

| | | | |
|---|---|---|---|
| 2,317,757 | 4/1943 | Graf | 564/473 |
| 4,152,353 | 5/1979 | Habermann | 564/446 |
| 4,190,601 | 2/1980 | Decker et al. | 564/473 |

FOREIGN PATENT DOCUMENTS 2545695 10/1975 Fed. Rep. of Germany .
2618580 11/1977 Fed. Rep. of Germany .
59-199655 11/1984 Japan .
60-130551 7/1985 Japan .

*Primary Examiner*—Glennon H. Hollrah
*Assistant Examiner*—Scott C. Rand

[57] ABSTRACT

A process for the preparation of permethylated amines, particularly pentamethyldiethylenetriamine, by the reductive methylation of diethylenetriamine in the presence of hydrogen, a nickel-containing catalyst, aqueous formaldehyde and methanol, comprising feeding continuously the formalehyde to the reaction system in two phases. In the first phase, a sufficient amount of formaldehyde to mono-methylate the primary amine groups present, is fed to the reaction system at a high flow rate, and thereafter the flow rate of the formaldehyde is substantially reduced, for the reductive methylation of the secondary amine groups. By this method the production of by-products is substantially reduced and preparation times are significantly shorter in comparison to processes where the formaldehyde flow rate remains constantly high for the entirety of the reaction.

14 Claims, No Drawings

METHOD FOR THE REDUCTIVE METHYLATION OF PRIMARY AMINES

FIELD OF THE INVENTION

This invention relates to the methylation of amines containing at least one primary amine group and has particular application in the production of permethylated amines.

BACKGROUND OF THE INVENTION

In general, methylated amines are prepared by the reductive methylation of a suitable amine, for example, diethylenetriamine, using a reductive methylation catalyst, formaldehyde, and hydrogen.

Hitherto, such reactions have been carried out at relatively high pressures, for example, from 50 to 200 bar. For example, DE 25 45 695-A and DE 26 18 580-A (BASF) both disclose reductive methylation processes, carried out at a pressure of 200 bar.

At such relatively high pressures, acceptably high yields can be obtained (for example from 90 to 95 percent) Commercially however, it is disadvantageous to utilize such high pressures, because of the need for relatively complex equipment an handling operations.

Japanese published Patent Application number 60-130551 discloses a low pressure process for the reductive methylation of amines, to produce tertiary amines. However, the process requires an expensive platinum or palladium catalyst.

It is the object of this invention to provide a method for the preparation of permethylated amines avoiding the use of complex high pressure equipment and expensive metal catalysts.

SUMMARY OF THE INVENTION

We have discovered that reductive methylation of primary amines can be carried out in relatively high yield and economically convenient reaction times at low pressures, for example at 50 bar or less, or even at pressures of 20 bar or less, without the need for expensive catalysts or high pressure equipment.

In one aspect, this invention is a method for the preparation of N-methylated amines by superatmospheric pressure reductive methylation of amines initially containing at least one primary amine group which comprises reacting the amine with formaldehyde and hydrogen in the presence of a reductive methylation catalyst, wherein formaldehyde is fed continuously to the reaction mixture and characterized in that the flow rate of formaldehyde to the reaction system is reduced after a stoichiometric amount of formaldehyde sufficient to mono-methylate the primary amine group in the first phase of the reaction has been fed but substantially before formaldehyde to methylate the so produced secondary amine groups is fed and wherein the flow rate to the reaction system is substantially reduced for the second phase during which a further quantity of formaldehyde sufficient to achieve complete methylation of the amine is fed.

Surprisingly, it is found that by conducting the reaction in such a way that the flow rate of the formaldehyde is reduced after the primary amine groups have been converted into secondary amine groups can result in the preparation of permethylated amines in good yields and purity. Formation of undesirable by-products is greatly decreased, as compared with conventional methods of operation, in which a constant formaldehyde flow rate is utilized. Further, the reaction time is greatly decreased in comparison to processes where the flow rate of the formaldehyde is held constant through the entirety of the preparation.

DETAILED DESCRIPTION OF THE INVENTION

As described hereinabove, this invention relates to the preparation of permethylated amines, and more particularly alkyl polyamines, wherein the flow rate of formaldehyde to the reaction system is reduced after the first phase consisting of mono-methylating the primary amine groups.

The extent to which the formaldehyde flow rate is reduced after the primary amine groups have been mono-methylated and converted into secondary amine groups is sufficient to result in substantially reduced by-product content in the resulting permethylated amines as compared to the same process wherein the aldehyde is supplied at a constant rate.

Typically, the reaction is carried out in two reaction rate phases, a first phase during which the stoichiometric amount of formaldehyde required for the mono-methylation of the said primary amine group(s) is fed to the reaction mixture at a substantially constant flow rate, and a second phase during which a further quantity of formaldehyde, sufficient to achieve complete methylation of all remaining amine hydrogens, is fed to the reaction system, at a flow rate substantially lower than the said substantially constant flow rate of the mono-methylation phase. Advantageously, the flow rate of formaldehyde to the reaction system during the first phase is reduced by at least about 50 percent, preferably from about 50 to about 97.5 percent, and more preferably from about 83 to about 90 percent, for the second phase of the reaction.

Reducing the flow rate by percentages lower than this does not offer the significant reduction in by-product formation. By-products formed include, for example, partly methylated amine, higher molecular weight products and lower molecular weight products. Reductions of flow rates greater than about 97.5 percent can be practiced but lead to very long overall reaction times.

It is important that the reduction of the flow rate of formaldehyde takes place when a stoichiometric quantity sufficient to mono-methylate the amine has been fed but substantially before any formaldehyde is fed that will give a permethylated product.

The duration of the first reductive methylation phase will depend on the overall reactivity of the primary amine groups and the number of primary amine groups to be reacted. The duration of the second phase depends on the reactivity of the secondary amine groups but is preferably from about 2 to about 40 times that of the first phase, more preferably from about 6 to about 12 times that of the first phase.

For economic reasons, the flow rate of the formaldehyde for the first phase of the reductive methylation reaction is advantageously at least 0.1, depending on the reactivity of the amine, preferably at least 0.25 and more preferably at least 0.5 mole of formaldehyde per mole of amine per hour. Although it is possible to prepare products using slower feed rates, overall conversion and processing time become too long to be of commercial interest.

By way of example, in the reductive methylation of diethylenetriamine to produce pentamethyldiethylenetriamine, an amount formaldehyde sufficient to mono-methylate the primary amine groups (40 percent of the stoichiometric quantity of formaldehyde employed) may be fed to the reaction system over a time period sufficient to achieve mono-methylation of the primary groups in the first phase of the reaction. Advantageously, this is from about 0.5 to about 4 hours, preferably from about 0.5 to about 2 hours. The remaining quantity of formaldehyde sufficient to achieve complete methylation of the remaining secondary amine groups is then fed in the second phase of the reaction. Advantageously, this duration of the second phase feed is from about 1 to about 40 hours, preferably from about 12 to about 20 hours depending on amine reactivity, and in most instances will be at least twice the period and preferably at least six times the period of the first phase.

Although the feed time for the first reaction period can be longer, such is not so commercially advantageous.

The method of the invention may be utilized for the preparation of various N-methylated aliphatic, acyclic, aromatic or heterocyclic amines which may also be monoamines or polyamines with primary and optionally secondary amine groups. No special restrictions are imposed on the amine compounds which can be used as raw material in the method according to the invention, provided that they have at least one primary amine group and that they will undergo reductive methylation. Optionally, the amine compound may contain one or more secondary amine groups. The amines for which the process is particularly suitable have in general from 1 to 30 carbon atoms and may be optionally substituted, the existing substituents of the amine can be branched or linear, and can include, for example, methyl, ethyl, isopropyl, phenyl and the like, and if the case arises may carry chemically reactive substituents which do not detrimentally affect the reductive methylation process, for example chlorine.

Some representative examples of suitable amines are methylamine, ethylamine, propylamine, cyclohexylamine, ethylenediamine, propylenediamine (all isomers), diethylenetriamine, triethylenetetramine, polyalkylene polyamines such as tetraethylenepentamine, pentaethylenehexamine, aminoalkylpiperazines such as aminoethylpiperazine, alkanolamines such as monoethanolamine and aminoethylethanolamine, aniline, toluidene diamine, naphthylamine, mixtures thereof and the like.

The term formaldehyde as used herein is intended to include within its scope both formaldehyde itself, and substances capable of decomposing to provide formaldehyde under the reaction conditions employed, for example trioxane and para-formaldehyde. The formaldehyde may be aqueous formalin or a formaldehyde solution in methanol. The formaldehyde concentration may be from about 30 to about 60 percent. Preferably, about 35 to about 37 percent aqueous formalin is used. The quantity of formaldehyde used is at least an equimolar quantity in relation to each reactive hydrogen of the amine. Generally, a quantity within the range of about 1.0 to about 1.2 times the equimolar quantity in relation to each reactive hydrogen carried by the amine is used. In the description of this present invention the term reactive hydrogen refers to hydrogens associated directly with the nitrogen atom of the primary or secondary amine and which will undergo reductive methylation.

The reaction is carried out in the presence of a reductive methylation catalyst, many of which are known. Such catalysts generally comprise Ni, Pd, Co, Pt, or Cu. In the process of this invention, the preferred catalysts are those comprising nickel, cobalt or copper, and most preferred are nickel catalysts. They may be employed as fixed bed catalysts or used in powdered form, whichever is convenient for the reactor and equipment available. Preferred nickel catalysts are those which are activated by relatively low temperatures, for example 80° C. to 120° C. Examples of suitable nickel-containing catalysts are the commercially available hydrogenation/hydrogenolysis catalysts sold under the trade names Ni 5132P and Ni 6458P by Harshaw Chemie (Nederland). The product Ni 5132P contains 64 percent by weight nickel on a proprietary support and has a surface area of 193m$^2$ g$^{-1}$ and the product Ni 6458P contains 57 percent nickel, with a surface area of 204m$^2$ g$^{-1}$.

The ratio of catalyst to amine will generally depend on the nature of the amine, its molecular weight and the catalyst employed, but is preferably within the range of about 0.1 to about 30 g, more preferably about 4.0 to about 8.0 g of catalyst/mole of amine. A lower catalyst concentration tends to reduce the hydrogenation rate to unacceptable levels, and thus lower the conversion. Higher catalyst concentrations increase the rate of hydrogenation, but tend to result in an increase in temperature, which results in unwanted side-reactions being favored, and thus an increased production of by-products.

The reaction is typically carried out at a temperature of from about 80° C. to about 150° C., preferably about 80° C. to about 120° C., and more preferably about 80° C. to about 100° C. Operating at higher reaction temperatures results in undesirable reaction products and at lower temperatures the rate of reaction can be very slow. The reaction is typically carried out at a pressure of about 3 to about 50 bar or less, preferably about 30 bar or less, and more preferably about 20 bar or less. If the reaction is conducted at higher pressures, the distinct advantage of greatly reduced by-product formation through specific control of the formaldehyde feed rate is no longer significant.

It is particularly preferred in the method of the invention that the reaction is carried out in the presence of a volatile organic solvent. The volatile organic solvent should be one in which all the reactants are soluble and one which can readily be removed from the mixture at the end of the reductive methylation reaction.

Suitable solvents are those having a boiling point of about 120° C. or less and include aliphatic alcohols. Especially preferred are the aliphatic primary alcohols which include, for example, methanol, ethanol, propan-1-ol or mixtures thereof. Such solvents are preferred, because of the relatively high solubility of hydrogen in them, as compared with water.

The ratio of the volatile organic solvent to the amine is preferably 0.75:1 to 1.5:1 by weight, more preferably from 1.0:1 to 1.4:1 by weight, most preferably about 1.2:1. The use of a volatile solvent enables the solvent to be readily removed by volatilization, to enable the product to be recovered.

The permethylated amines prepared in accordance with the method of the invention, after purification by distillation or extraction, may be prepared in a purity of from 90 to 99 percent.

The methylated amine compounds prepared in accordance with the process of this invention are useful industrial chemicals which can be applied in a wide application range, as intermediates for agricultural chemicals and medicines, as foaming catalysts for polyurethanes and curing agents for epoxy resins, emulsifying agents, dispersing agents, corrosion prevention agents, auxiliary agents for textile dyeing and as washing aids for example in the preparation of synthesis gas.

A number of preferred embodiments of the invention are described in the following examples. Unless otherwise stated, all quantities are parts or percentage by weight.

EXAMPLE 1

A stainless steel autoclave (Haage) is charged with 10 parts of water, 10 parts of a nickel catalyst sold by Harshaw Chemie under the tradename Ni 6458P, 200 parts of diethylenetriamine and 240 parts of methanol.

The autoclave is purged with nitrogen and hydrogen and then pressurized with hydrogen, to a pressure of about 17 bar. The contents are then heated to 85° C. and maintained at this temperature for a period of half an hour, at a pressure of about 19 bar.

A 37 percent solution of formaldehyde in water, containing about 10 percent of methanol as a stabilizing agent, is then pumped into the reactor at a feed rate of 315 parts/hr for a period of about 1 hour.

The formaldehyde feed rate is then reduced to a rate of 38.7 parts/hr, and a further 542 parts of the same formaldehyde solution is fed to the reaction system, over a period of about 14 hours, at a constant rate.

Samples are taken throughout the reaction and analyzed by gas chromatography, after sedimentation of catalyst, to monitor the progress of the reaction.

After a total of 858 parts of formaldehyde have been fed to the autoclave, the process provides a yield of pentamethyldiethylenetriamine on the basis of total organics (excluding methanol and formaldehyde), of 89.8 percent.

As can be seen, when the formaldehyde feed rate for the second phase is approximately ⅛ that of the first phase, the product in good yield and purity is obtained.

EXAMPLE 2

An autoclave is charged with 200 parts of diethylenetriamine, 10 parts of the nickel-containing catalyst Ni 6458P and 300 parts of water. The autoclave is then purged with nitrogen and hydrogen and then pressurized with hydrogen to a pressure of 17 bar. The contents are then heated to a temperature of 85° C. and maintained at this temperature for a period of about 30 minutes.

A 37 percent solution of formaldehyde in water, containing about 10 percent of methanol as a stabilizing agent, is then pumped into the reactor at a flow rate of 118 parts/hr for a period of about 2.5 hours.

After 295 parts of formaldehyde solution (37 percent of the stoichiometric amount required to give the permethylated product) has been fed, the formaldehyde flow rate is reduced to a rate of 56 parts/hr. A further 618 parts of the same formaldehyde solution are then fed to the reaction over a period of about 11 hours.

At the end of the reaction, analysis of the products (excluding water and formaldehyde) showed the following product distribution: 29.4 percent partly methylated diethylenetriamine, 20.6 percent high molecular weight products, 5.7 percent low molecular weight products and 44.3 percent pentamethyldiethylenetriamine.

Reducing the flow rate of formaldehyde by only a factor of two when the stoichiometric amount of formaldehyde to give the mono-methylated product has been fed can substantially improve the reaction yields.

COMPARATIVE EXAMPLE A

This example demonstrates the greatly inferior yield and purity when formaldehyde is continued to be fed at a high flow rate after the mono-methylation of the primary amines has been effected.

A stainless steel autoclave (Haage) is charged with 10 parts of water, 10 parts of a nickel catalyst sold by Harshaw Chemie under the tradename Ni 6458P, 200 parts of diethylenetriamine and 240 parts of methanol.

The autoclave is purged with nitrogen and hydrogen and then pressurized with hydrogen, to a pressure of about 17 bar. The contents are then heated to 85° C. and maintained at this temperature for a period of half an hour, at a pressure of about 19 bar.

A 37 percent solution of formaldehyde in water, containing about 10 percent of methanol as a stabilizing agent, is then pumped into the reactor at a flow rate of 315 parts/hr for a period of about 1.5 hours.

After 481 parts of formaldehyde (60 percent of the stoichiometric amount required to give the permethylated product) has been fed, the formaldehyde flow rate is reduced to 56 parts/hr and a further 445 parts of the same formaldehyde solution is fed to the reaction over a period of about 8 hours.

After a total of 926 parts of formaldehyde have been fed to the autoclave, the process provides a yield of pentamethyldiethylenetriamine on the basis of total organics (excluding methanol and formaldehyde), of 17.5 percent. In addition 29.9 percent partly methylated diethylenetriamine, 43.1 percent high molecular weight products and 9.5 percent low molecular weight products are produced.

Even though the flow rate of formaldehyde is reduced by about 82 percent for the second feeding phase, there are substantial levels of undesirable by-products present as the high feed rate of formaldehyde is continued after the stoichiometric quantity to mono-methylate the amine has been fed.

COMPARATIVE EXAMPLE B

This comparative example illustrates the lower yields and purity of permethylated product obtained when formaldehyde is fed at a slow and constant feed rate for the entirety of the preparation.

An autoclave is charged and prepared as in Example 2.

A 37 percent solution of formaldehyde in water, containing about 10 percent of methanol as a stabilizing agent is then pumped into the reactor at a flow rate of 36.5 parts/hr for a period of about 22.7 hours, until a total of about 829 parts formaldehyde has been fed.

At the end of the reaction, analysis of the products (excluding water and formaldehyde) shows the following product distribution: 1.5 percent partly methylated diethylenetriamine, 11.4 percent high molecular weight products, 4.6 percent low molecular weight products and 82.6 percent pentamethyldiethylenetriamine.

As can be seen from these examples, the employment of a low pressure process wherein the formaldehyde solution is fed at two different flow rates is advantageous for the yield and purity of the permethylated product.

The importance of changing the flow rate at the point where mono-methylation is achieved, stoichiometrically, is clearly illustrated. In addition, the importance of the magnitude in the difference between the first and second phase flow rate is clearly demonstrated.

What is claimed is:

1. A method for the preparation of permethylatedamines by superatmospheric pressure reductive methylation of amines initially containing at least one primary amine group which comprises reacting the amine with formaldehyde and hydrogen in the presence of a reductive methylation catalyst, wherein formaldehyde is fed continuously to the reaction mixture and characterized in that the flow rate of formaldehyde to the reaction system is reduced after a stoichiometric amount of formaldehyde sufficient to mono-methylate the primary amine groups in the first phase of the reaction has been fed but substantially before formaldehyde to methylate the so produced secondary amine groups is fed and wherein the flow rate to the reaction system is substantially reduced for the second phase during which a further quantity of formaldehyde sufficient to achieve complete methylation of the amine is fed.

2. The method as in claim 1 wherein the amine is an alkyl polyamine and optionally containing secondary amine groups.

3. The method as in claim 1 wherein the flow rate of formaldehyde for the first phase of the reaction is reduced by at least 50 percent for the second phase of the reaction.

4. The method as in claim 3 wherein the duration of the second phase is from 2 to 40 times that of the first phase.

5. The method as in claim 4 wherein the duration of the second phase is from 6 to 12 times that of the first phase.

6. The method as in claims 1 wherein the reaction is carried out in the presence of a volatile organic solvent.

7. The method as in claim 6 wherein the volatile organic solvent is a primary alcohol.

8. The method as in claim 7 wherein the volatile organic solvent is methanol.

9. The method as in claim 1 wherein the amine is ethylenediamine, diethylenetriamine, aminoethylpiperazine, triethylenetetramine, monoethanolamine, aminoethylethanolamine, tetraethylenepentamine, pentaethylenehexamine, or mixtures thereof.

10. The method as in claim 9 wherein the amine is diethylenetriamine.

11. The method as in claim 1 wherein the reaction is carried out at a temperature of not more than 150° C.

12. The method as in claim 1 wherein the reaction is carried out at a pressure of not more than 50 bar.

13. The method as in claim 1 wherein the reaction is carried out at a pressure of not more than 20 bar.

14. The method as in claim 1 wherein the amine is diethylenetriamine and the formaldehyde is fed continuously to the reaction mixture in two steps where the said first step consists of mono-methylating the primary amine groups present and the second step consists of methylating the secondary amine groups present in a period of time that is from 6 to 12 times that of the first step, and where the reaction pressure does not exceed 20 bar and the reaction temperature 150° C.

* * * * *